United States Patent [19]

Johnson

[11] 4,244,875
[45] Jan. 13, 1981

[54] 2-DECARBOXY-2-HYDROXYMETHYL-9-DEOXY-5,9α-EPOXY-4,5-CIS-17,18-TETRADEHYDRO-PGF$_1$ COMPOUNDS

[75] Inventor: Roy A. Johnson, Kalamazoo, Mich.

[73] Assignee: The Upjohn Company, Kalamazoo, Mich.

[21] Appl. No.: 73,457

[22] Filed: Sep. 7, 1979

Related U.S. Application Data

[60] Division of Ser. No. 932,982, Aug. 11, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.$^3$ ............................................. C07D 311/02
[52] U.S. Cl. ................................. 260/345.2; 424/283
[58] Field of Search ..................................... 260/345.2

[56] References Cited

U.S. PATENT DOCUMENTS 4,125,713  11/1978  Nelson ................................ 542/426

*Primary Examiner*—Nicky Chan
*Attorney, Agent, or Firm*—Robert A. Armitage

[57] ABSTRACT

The present invention relates to novel 2-decarboxy-2-hydroxymethyl-9-deoxy-5,9α-epoxy-4,5-cis-17,18-tetradehydro-PGF$_1$ compounds, which are useful for inducing a variety of prostacyclin-like pharmacological effects. Accordingly, these compounds are useful pharmacological agents for the same purposes for which prostacyclin is employed.

12 Claims, No Drawings

2-DECARBOXY-2-HYDROXYMETHYL-9-DEOXY-5,9α-EPOXY-4,5-CIS-17,18-TETRADEHYDRO-PGF₁ COMPOUNDS

DESCRIPTION

CROSS REFERENCE TO RELATED APPLICATION

The present application is a divisional application of U.S. Ser. No. 932,982, filed Aug. 11, 1978, now pending issuance as a United States patent; which is a divisional application of U.S. Ser. No. 819,856, filed July 28, 1977, now U.S. Pat. No. 4,123,441; which is a continuation-in-part application of U.S. Ser. No. 725,546, filed Sept. 22, 1976, now abandoned; which is a continuation-in-part application of U.S. Ser. No. 716,960, filed Aug. 23, 1976, now abandoned.

BACKGROUND OF THE INVENTION

The present invention relates to novel 2-decarboxy-2-hydroxymethyl-9-deoxy-5,9α-epoxy-4,5-cis-17,18-tetradehydro-PGF₁ compounds, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention is incorporated here by reference from U.S. Pat. No. 4,123,441.

SUMMARY OF THE INVENTION

The present invention particularly provides: a compound of the formula

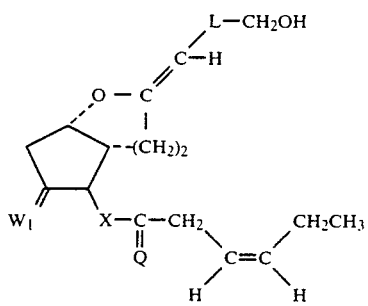

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;
wherein L is
(1) —(CH$_2$)$_d$—C(R$_2$)$_2$, or
(2) —CH=CH—,
wherein d is zero to 5, R$_2$ is hydrogen, methyl, or fluoro, being the same or different with the proviso that one R$_2$ is not methyl when the other is fluoro,
wherein Q is oxo, $\alpha$—H:$\beta$—H, $\alpha$—OH:$\beta$—R$_8$ or $\alpha$—R$_8$:$\beta$—OH
wherein R$_8$ is hydrogen or alkyl of one to 4 carbon atoms, inclusive; and
wherein X is
(1) trans—CH=CH—,
(2) cis—CH=CH—,
(3) —C≡C—, or
(4) —CH$_2$CH$_2$—;
including the lower alkanoates thereof.

With regard to the divalent substituents described in the claims, e.g., Q and W$_1$, these divalent radicals are defined as $\alpha$—R$_i$:$\beta$—R$_j$, where R$_i$ represents a substituent of the divalent moiety of the alpha configuration with respect to the cyclopentane and R$_j$ represents a substituent of the divalent moiety of the beta configuration with respect to the cyclopentane ring. Accordingly, when Q is defined as $\alpha$—OH:$\beta$—R$_8$, the hydroxy of the Q moiety is in the alpha configuration, i.e., as in prostacyclin, and the R$_8$ substituent is in the beta configuration. Not all carbon atoms to which such divalent moieties are attached represent asymmetric centers. For example, when both valence bonds are to hydrogen (e.g., W$_1$ or Q is $\alpha$—H:$\beta$—H), then no asymmetric center is present.

DESCRIPTION OF THE PREFERRED EMBODIMENTS

The present invention particularly relates to the following chemical compounds:
2-Decarboxy-2-hydroxymethyl-(4Z)-9-deoxy-5,9α-epoxy-Δ4-11-deoxy-cis-17,18-didehydro-PGF₁;
2-Decarboxy-2-hydroxymethyl-(4Z)-9-deoxy-5,9α-epoxy-Δ4-13,14-dihydro-cis-17,18-didehydro-PGF₁;
2-Decarboxy-2-hydroxymethyl-(4Z)-9-deoxy-5,9α-epoxy-Δ4-15-keto-cis-17,18-didehydro-PGF₁; and
2-Decarboxy-2-hydroxymethyl-(4Z)-9-deoxy-5,9α-epoxy-Δ4-15-deoxy-cis-17,18-didehydro-PGF₁.

I claim:

1. A compound of the formula

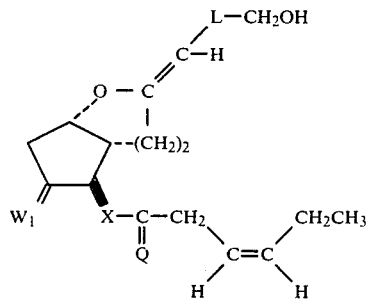

wherein W$_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;
wherein L is
(1) —(CH$_2$)$_d$—C(R$_2$)$_2$, or
(2) —CH=CH—,
wherein d is zero to 5, R$_2$ is hydrogen, methyl, or fluoro, being the same or different with the proviso that one R$_2$ is not methyl when the other is fluoro,
wherein Q is oxo, $\alpha$—H:$\beta$—H, $\alpha$—OH:$\beta$—R$_8$ or $\alpha$—R$_8$:$\beta$—OH
wherein R$_8$ is hydrogen or alkyl of one to 4 carbon atoms, inclusive; and
wherein X is
(1) trans—CH=CH—,
(2) cis—CH=CH—,
(3) —C≡C—, or
(4) —CH$_2$CH$_2$—;
including the lower alkanoates thereof.

2. A compound according to claim 1, wherein W$_1$ is $\alpha$—H:$\beta$—OH.

3. A compound according to claim 1, wherein W$_1$ is oxo.

4. A compound according to claim 1, wherein W$_1$ is methylene.

5. A compound according to claim 1, wherein $W_1$ is $\alpha$—H:$\beta$—H.

6. A compound according to claim 5, wherein L is —$(CH_2)_n$—, n being 2, 3, or 4, wherein Q is oxo or $\alpha$—OH:$\beta$—$R_8$ and wherein $R_8$ is hydrogen, methyl, or ethyl.

7. A compound according to claim 1, wherein $W_1$ is $\alpha$—$CH_2OH$:$\beta$—H.

8. A compound according to claim 1, wherein $W_1$ is $\alpha$—OH:$\beta$—H.

9. A compound according to claim 8, wherein L is —$(CH_2)_n$—, n being 2, 3, or 4, wherein Q is oxo or $\alpha$—OH:$\beta$—$R_8$ and wherein $R_8$ is hydrogen, methyl, or ethyl.

10. A compound according to claim 9, wherein X is —C≡C—.

11. A compound according to claim 9, wherein X is —$CH_2CH_2$—.

12. A compound according to claim 9, wherein X is trans—CH=CH—.

* * * * *